US005508498A

United States Patent [19]
Rheinish et al.

[11] Patent Number: 5,508,498
[45] Date of Patent: Apr. 16, 1996

[54] MICROWAVE HEATING UTENSIL

[75] Inventors: Robert S. Rheinish, Trabuco Canyon; Yading Wang, South Pasadena, both of Calif.

[73] Assignee: Invenetics LLC, Trabuco Canyon, Calif.

[21] Appl. No.: 318,276

[22] Filed: Oct. 5, 1994

[51] Int. Cl.$^6$ .................................................. H05B 6/80
[52] U.S. Cl. .................... 219/730; 219/759; 99/DIG. 14; 426/243; 426/109
[58] Field of Search .................................... 219/730, 759; 99/DIG. 14; 426/107, 109, 241, 243

[56] References Cited

U.S. PATENT DOCUMENTS

| | | | |
|---|---|---|---|
| 4,743,726 | 5/1988 | Hughes et al. | 219/759 |
| 4,914,717 | 4/1990 | Gibbon | 219/759 |
| 4,931,608 | 6/1990 | Bills | 219/730 |
| 4,933,193 | 6/1990 | Fisher | 219/730 |
| 4,963,708 | 10/1990 | Kearns et al. | 219/730 |
| 4,983,798 | 1/1991 | Eckler et al. | 219/759 |
| 5,006,405 | 4/1991 | Watkins et al. | 428/323 |
| 5,070,223 | 12/1991 | Colasante | 219/759 |

FOREIGN PATENT DOCUMENTS 0276654  10/1994   European Pat. Off. .......... H05B 6/64

OTHER PUBLICATIONS

GE Publication, Feb. 1991, GE Silicones/Food Contract Applications Silicone Rubber Compounds.
GE Publication, Feb. 1992, GE Silicones/Underwriters+ Laboratories Recognition for Silicone Rubber Adhesive Sealants.
GE Publication, Oct. 1982, GE Silicones/One–Component RTV Adhesive Sealants.

Primary Examiner—Philip H. Leung
Attorney, Agent, or Firm—Poms, Smith, Lande & Rose

[57] ABSTRACT

A utensil for use, for example, in the home or in restaurants, with a microwave oven for heating food preparation or service vessels (such as a dinner plate) and the food in such vessels. The utensil includes a matrix material and a microwave absorptive material. The utensil may also be configured for direct conductive heat transfer heating of food into which the utensil is immersed. Alternatively, an appliance for applying therapeutic dry or moist heat to the human body may use pellets of the matrix and microwave absorptive material in a flexible moisture and heat transmissive body.

13 Claims, 2 Drawing Sheets

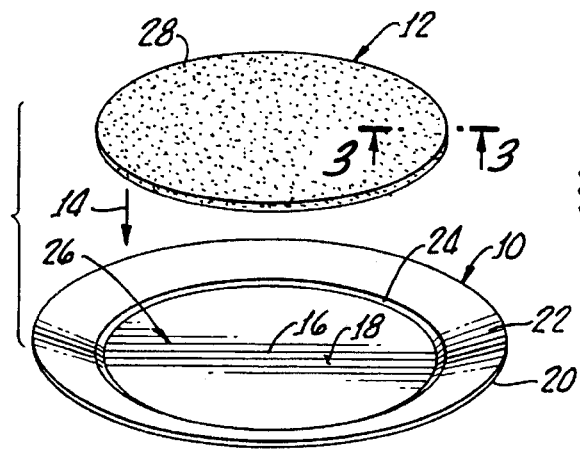
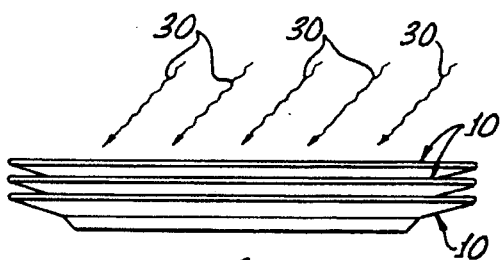
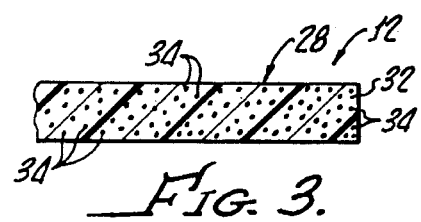
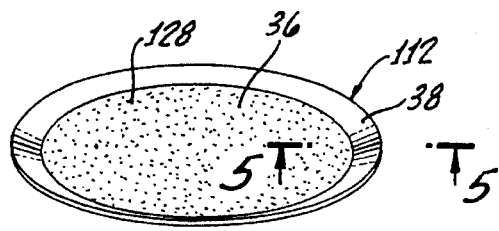
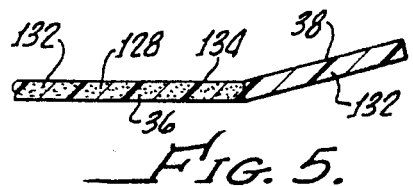
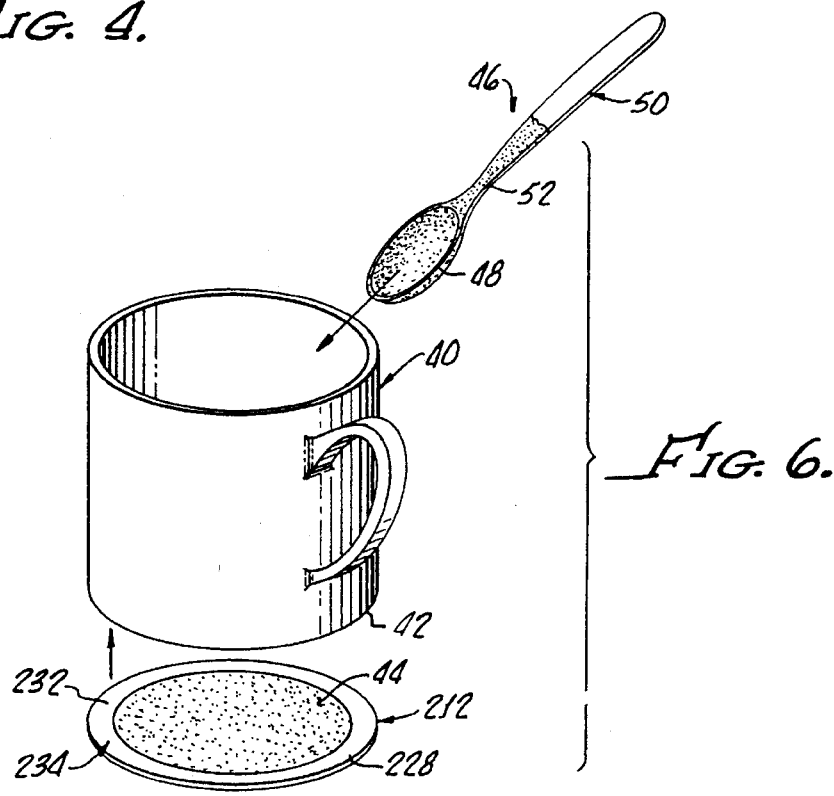

MICROWAVE HEATING UTENSIL

BACKGROUND OF THE INVENTION

1. Field of the Invention

The present invention is primarily in the field of utensils for use in the home in food preparation with a microwave oven. The utensils may be used to prepare food for consumption, or to warm service ware, such as dinner plates upon which food is to be served. For example, the utensil may take the form of a spoon-like article which is immersed in food in a container while this food is being heated in a microwave oven. The spoon-like article absorbs microwave energy more effectively than does the food, and transfers heat to the food by conduction for faster warming of the food in the microwave oven. Alternatively, the utensil may take the form of a disk-like article for attachment to a container in which food is heated in a microwave oven. Again, the attached utensil absorbs microwaves more effectively than the container or the food therein, and transfers heat to the food via the container.

Also, a utensil according to the present invention may be used to quickly warm other food serving utensils, such as dinner plates or soup bowls, for example. Such warmed dinner plates or soup bowls, for example, help preserve the warmth of food placed into them until the food can be served for consumption.

Alternatively, a utensil according to the present invention may take the form of a ball of spheroid (i.e., pellet), which singularly or in multitudes may be heated in a microwave oven. Such a ball or spheroid may be placed into a quantity of food for increasing the speed with which the food will heat in a microwave oven similarly to the spoon-like article. Still alternatively, a multitude of such spheroid pellets may be placed into a flexible heat-transmissive container and heated in a microwave oven. The container may be configured like a pad or wrap for the human body. After heating, the flexible container may be applied to the body of a person as a hot pad or hot wrap for therapeutic heating purposes. This pad or wrap may combine the advantages of moist heat for additional therapeutic effect.

2. Related Technology

A conventional cooking utensil for use in microwave ovens is known in accord with U.S. Pat. No. 5,107,087, issued 21 Apr. 1992 to Katsuya Mamda, et al. The '087 patent is believed to disclose a cooking grill-like utensil in which a metal plate is provided on its upper surface with a layer of non-stick material, and on a lower surface is provided with a layer of heat buildup material. The heat buildup material is absorptive of microwaves so that this material heats the metal plate by conduction and allows food to be cooked on the upper non-stick surface. A covering permeable to microwaves is provided on the heat buildup layer, and also defines legs for supporting the utensil in a microwave oven. A removable cover (like a lid for the grill) is reflective of microwaves to prevent the food from being heated directly.

A conventional cooking film for use with a microwave oven to prepare food is known in accord with European patent application publication No. 0 276 654, published 3 August 1988 (03 08 88), on application No. 88100112.7. This publication is believed to disclose a receptor film for use in a microwave oven to brown or crisp food wrapped in the film. The film is formed of cross-linkable and heat resistant resin with microwave-interactive particles.

A conventional microwave-heatable sheet for food packaging is known in accordance with U.S. Pat. No. 5,006,405, issued 9 April 1991, The '405 patent is believed to disclose a sheet with a smooth coating on a paper or paperboard backing. On the smooth coating, a layer of microwave interactive material is carried. This microwave interactive coating can include carbon or a semi-conductive metallic coating.

As is well known, many food items are best served on a heated dinner plate. This heating of dinner plates helps preserve the warmth of the food, and prevent its cooling off before the food can be served and consumed. Further, many food items are low in moisture content, and are also low in heat content. These foods especially do not warm well in a microwave oven, and cool off quickly losing some of their appeal and taste if placed on a cool dinner plate for service. Also, when using a microwave oven to warm food, in a cup or bowl for example, some food items because of their low moisture content do not heat well. Also, even some foods which have a high moisture content do not heat as well as desired in a microwave oven. These foods, such as water for tea or coffee, or milk for hot cocoa, for example, take longer than desired to heat in a microwave oven because of the high heat capacity of the water or milk itself.

However, none of the microwave heating films or appliances conventionally known are intended for or are adequate for allowing the heating of bowls, mugs, cups, or only of the central food-contacting portion of dinner plates, for example, in a microwave oven. Such heating of dinner plates, for example, is a desirable facility because many food items are best served on a warm dinner plate. However, the usual means by which dinner plates are warmed in preparation for food service is to heat them in an oven. Restaurants generally have an oven or dedicated dinner plate heater for this purpose. However, the home kitchen seldom has more than a single, or sometimes two, conventional ovens available for use. In each case, when an oven or dedicated plate heater is used to heat dinner plates, the entire plate gets hot. As a result, service personnel handling the hot plates, and guests or patrons of a restaurant, for example, are at risk of being burned by the hot plates. Also, the energy waste resulting from such a use of an oven or dedicated plate heater is considerable. Further, in the preparation of food for a large group or dinner party, for example, all of the available ovens will be devoted to food preparation. Thus, a considerable problem of logistics is presented in order to prepare the food for the group, while still providing heated dinner plates upon which to serve the food. If a microwave oven is available, an attempt might be made to heat the dinner plates prior to the food being placed on them for service.

However, most dinner plates are formed of glass, china, ceramic, or plastic materials, none of which heat well in a microwave oven. Further, if an attempt is made to heat such dinner plates in a microwave oven, the poor heating quality of the plates may tempt the user to use a high power setting and/or an extended interval of heating. Unfortunately, many dinner plates do include decorations, such as metallic (gold or silver, for example) bands, filigrees, or other such ornate patterns. This metallic decoration will heat in a microwave oven. Moreover, if the user of the oven attempts to heat such a dinner plate by applying a high power or prolonged interval of oven operation, the dinner plates may be damaged by having their decorative metallic trim overheated and damaged. A utensil which would allow dinner plates to be quickly and efficiently heated in a microwave oven without damage would have considerable utility, and be greatly desired.

Further, a utensil which could be used directly with food to be heated in a microwave oven, or which could be attached to a vessel in which the food was heated in order to improve the efficiency of microwave absorption and transfer of heat to the food would also be desired.

Still further, an article which could be heated in a microwave oven, either dry or with water to provide moist heating for therapeutic purposes, would be desirable.

SUMMARY OF THE INVENTION

In view of the deficiencies of the related technology, a primary object for this invention is to provide a microwave heating utensil which allows food service or preparation utensils, such as a dinner plate, bowl, mug, or cup, for example, to be quickly warmed in a microwave oven.

Further, an object of this invention is to provide an article which may be placed directly into food in a container which is to be heated in a microwave oven, which article is a more efficient absorber of microwave energy than the food, and which conducts heat to the food to shorten its heating time in a microwave oven.

Additionally, an object of this invention is to provide an article which will quickly heat in a microwave oven either dry, or with water to provide moist heat, and which is configured for application to the body for therapeutic purposes.

In view of the above, the present invention provides a microwave heating utensil particularly for heating dinner plates or other food-service or preparation vessels in a microwave oven, the utensil including a flexible body of matrix material, and a microwave absorber material carried in the matrix and effective upon exposure of the utensil to microwave energy to heat the matrix, the body of the utensil defining a heat-transfer surface for conducting heat outwardly of the utensil to a dinner plate or other food-service or preparation vessel and having a large ratio of heat-transfer surface area to volume.

According to another aspect, the present invention provides a microwave heating utensil particularly for direct heat-transfer immersion heating of food in a container, the utensil including a body of matrix material, and a microwave absorber material carried in the matrix material body and effective upon exposure of the utensil to microwave energy to heat the matrix, the body defining a heat-transfer surface for conducting heat outwardly of the utensil directly to the food in the container in which the utensil is immersed.

Still further, the present invention according to another aspect thereof provides a method of heating dinner plates preparatory to the serving of food on the dinner plates for consumption, the method including the steps of heating a central food-contacting portion of the dinner plates; and maintaining a rim portion of the dinner plates substantially unheated.

Another aspect of the present invention provides a flexible therapeutic heating wrap for use on the human body to provide either dry or moist heat, the wrap including a flexible moisture-transmissive and heat-transmissive hollow body defining a chamber therewithin, and a plurality of microwave absorptive pellets disposed in and substantially filling the chamber of the hollow body, the microwave absorptive pellets including a water-tolerant matrix material and a microwave absorptive material.

Additional objects and advantages of the present invention will be apparent in view of the following description of several exemplary preferred embodiments of the invention, taken in conjunction with the following drawing Figures, as are briefly described below.

BRIEF DESCRIPTION OF THE DRAWING FIGURES

FIG. 1 presents an exploded perspective view of a microwave heating utensil embodying the principles of the present invention along with a dinner plate which is to be heated with the utensil in a microwave oven;

FIG. 2 provides a side elevation view of a stack of dinner plates like the one seen in FIG. 1, each one of which carries a respective microwave heating utensil, and which is being heated in a microwave oven.

FIG. 3 is an enlarged fragmentary cross sectional view take at line 3—3 of FIG. 1;

FIG. 4 provides a perspective view of an alternative embodiment of a microwave heating utensil according to the present invention;

FIG. 5 is an enlarged fragmentary cross sectional view taken at line 5—5 of FIG. 4;

FIG. 6 provides a perspective view of a transparent glass mug into which a spoon-like microwave heating utensil is about to be placed, and to the lower bottom surface of which a microwave heating utensil is about to be attached, all preparatory to heating contents of the mug in a microwave oven;

FIG. 7 is a fragmentary front elevation view of a person using a therapeutic microwave heating article according to the present invention;

FIG. 8 provides a plan view of the therapeutic microwave heating article seen in FIG. 7; and FIG. 9 is a fragmentary cross sectional view taken along ling 9—9 of FIG. 8.

DETAILED DESCRIPTION OF THE EXEMPLARY EMBODIMENTS OF THE INVENTION

Figure 7:
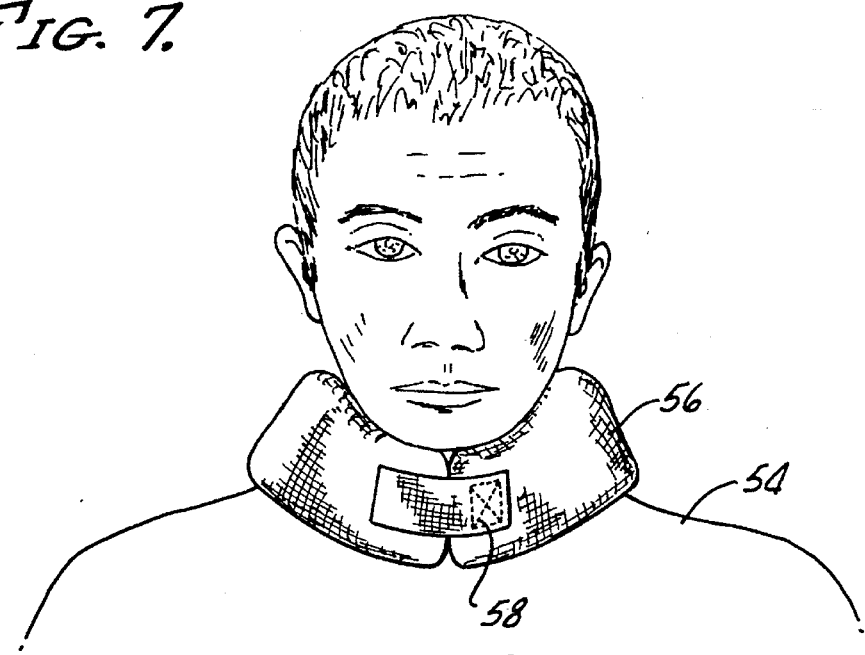

FIG. 1 presents a perspective view of a dinner plate 10 upon which a microwave heating utensil 12 according to the invention is being placed, as is indicated by the arrow 14. It will be seen that the dinner plate 10 includes a central, generally flat and circular, food contacting portion 16 having a surface 18, and an angulated circumferential rim portion 20 having a surface 22. The surfaces 18 and 22 are connected to one another by a circumferential and generally vertically angulated transition surface 24 so that a shallow recess 26 is presented by the dinner plate 10 for retaining food and associated liquids upon the surface 18 of central portion 16.

Viewing the utensil 12, it is seen that this utensil includes a generally flat and disk-like body 28. Generally the body 28 is shape retaining, but is sufficiently flexible that it will easily conform to the surface 18 of the dinner plate 10. The body 28 is circular like the recess 26 of the dinner plate 10, and is sized to fit in this recess. FIG. 2 shows that a stack of plural plates 10 (each one of which carries a respective heating utensil 12 as seen in FIG. 1) is heated in a microwave oven (not shown, but indicated with the arrows 30). The heating utensils 12 each efficiently absorb microwave energy and become hot. Heat from the heating utensils 12 is transferred by conduction to the central food-contacting surface 18 of the plates 10. Accordingly, the central food-contacting portion 16 of each plate 10 is quickly and efficiently heated. However, because the materials from which dinner plates are formed (glass, ceramic, china, plastic, etc.) are not very good conductors of heat, the rim portions 20 of the plates 10 remains relatively cool. Further, because the utensils 12 absorb microwave energy, heat, and transfer heat to the plates 10 efficiently by conduction, the energy level and duration of energy application may be low enough that the decorations and filigrees (if any) on the plates 10 are not heated sufficiently to be damaged by the microwaves.

Viewing FIG. 3, it is seen that the body 28 of the utensil 12 includes a flexible but shape-retaining matrix of electrically non-conductive material 32. The body 28 may alternatively be made of rigid matrix material, or of matrix material which is substantially rigid at room temperature but which softens and becomes conformal to the surface of a dinner plate when warmed by microwave heating. A sufficient heat-transfer surface area contact between the body 28 and the surface of a dinner plate, for example, can be achieved regardless of whether the body 28 is rigid, heat-softening, or flexible. For example, the body 28 may be formed of a rigid or heat-softening resinous polymeric material within the ambit of the present invention. Preferably, the matrix material 32 is a silicone rubber which is rated for repeated food contact by the Food and Drug Administration (FDA). For example, one such material is marketed by General Electric as the RTV102, RTV103, RTV106, RTV108, RTV109, RTV112, RTV116, and RTV118, family of one-component, ready-to-use silicone rubbers. An FDA approved Dow Corning silicone rubber may be used also in the formation of the matrix 32 of body 28. This body 28 is preferably 0.25 mm to about 5 mm thick. Substantially uniformly dispersed in the matrix 32 is a granular, fibrous, filamentary or powder microwave energy absorber material, generally indicated with the numeral 34 on FIG. 3. The material 34 is an efficient absorber of microwave energy.

Preferably, the material 34 is selected from the group of materials including graphite powder or granules, iron powder or filings, steel powder or filings, ferrite powder or granules, copper or aluminum particles, activated carbon powder and carbon black in powder or granular form. Each of these materials, and other materials, may also be employed in a fibrous or filamentary form. Preferably, the material 34 is present in the form of particles having a size of less than about 600 microns. However, the material 34 may be used in powder or granular form with a size from as little as 1 micron, or smaller, in size up to a size of about 1 mm, or larger. Also preferably, the material 34 is present in the matrix 32 to a percentage of from about 1 percent or less to about 80 percent or more, on a weight basis dependent upon the particular microwave absorber material selected and the desired heating rate with a view to the available power from various microwave ovens to be used.

Dependent upon the heat transfer coefficient of the matrix material 32 (which is known from the literature about this material, or which may otherwise be established), and the microwave absorption of the selected dispersed microwave energy absorber material 34, the percentage of the material 34 in the matrix 32 may be selected so that a utensil 12 may be continuously heated at the highest power setting available with a particular oven without generating a temperature in the matrix 32 sufficient to char the matrix material. That is, the percentage of the absorber material 34 will vary dependent upon the wattage of the oven or ovens in which the utensils 12 are to be used.

It will be noted that the matrix material 32 is electrically non-conductive, or is an insulator. Thus, any differential voltages which appear on the particles of dispersed absorber material 34 are insulated from one another, and sparking does not generally occur in the utensil 12. Similarly, this matrix material 32 is not a particularly good conductor of heat. However, when the utensil 12 is heated on the surface 18 of the plate 10, the large contacting surface area and comparative thinness of the utensil 10 insures that heat is efficiently conducted to the plate. In other words, the utensil 10 has a high ratio of heat-transfer surface area with the dinner plate surface 18 compared to the volume of the utensil. Thus, the central food-contacting portion 16 of the plate 10 is heated, while the rim portion 20 of the plates 10 remain cool. In this respect, the shape-retaining flexible and surface-conforming nature of the utensil 12 is important. This characteristic of the utensil 12 insures intimate heat-transfer relationship between the utensil 12 and the food-contacting portion 16 of the plate 10.

After the plates 10 are heated in a microwave oven, recalling FIG. 2, the stack of heated plates (and each plate 10 individually) may be conveniently handled by the still-cool rim portion 20. The fact that the rim portion 20 remains cool while the center food-contacting portion 16 of the plates 10 is hot is an important safety factor in preventing burns both to service personnel and to guests who are served food on the warmed plates 10. In order to prepare the heated plates for receiving food to be served, the utensils 12 are removed from the central food-contacting portions 16. Because the matrix material 32 is not a very good conductor of heat, and because the thermal capacity of the utensil 12 is itself not very high, the utensils 12 may generally be grasp with the bare fingers to remove the utensils from the plates 10.

However, FIGS. 4 and 5 illustrates an alternative embodiment of the present invention in which a non-heating peripheral portion is provided on a utensil for the purpose of making removal of the utensil from a hot dinner plate easier, along with reducing the risk of tender fingers contacting the hot surface of a dinner plate. In order to obtain reference numerals for use in describing the embodiment depicted in FIG. 4, features which are the same or which are analogous in structure or function to those depicted and described above are referenced with the same numeral used above and increased by one-hundred (100). Viewing FIGS. 4 and 5, a heating utensil 112 includes a generally round body 128 which includes a continuous matrix material 132. However, the matrix material 132 is not substantially homogenous like that of the embodiment of FIGS. 1–3. That is, the matrix material does not include a substantially uniform dispersion of microwave absorber material 134. The microwave absorber material 134 of the embodiment seen in FIGS. 4 and 5 is dispersed substantially uniformly in a central area 36 of the body 128. However, the body 128 includes a peripheral rim portion 38 which includes the matrix material 132, but does not include any of the microwave absorber material 134. Consequently, the rim portion 38 of the utensil 112 does not heat when the utensil is exposed to microwave energy. This rim 38 remains cool so that a user of the utensil can more easily remove the utensil from heated plates.

Still further, as FIG. 5 best shows, the rim portion 38 is angulated or cone shaped relative to the substantially flat remainder of the utensil 112. Thus, when the utensil 112 is placed on a dinner plate and the plate is heated in a microwave oven by use of the utensil 112, after this heating the user may simply grasp the upstanding angulated rim portion 38 in order to lift the utensil from the plate. The user's fingers need never touch the underlying heated central food-contacting surface of the dinner plate. Of course, as with the embodiment of FIGS. 1–3, the embodiment of FIGS. 4 and 5 results in the center of dinner plates being heated with the rim of the plates remaining comfortably cool for handling of the plates.

Viewing now FIG. 6, two additional embodiments of the present invention are depicted in this one drawing Figure. In order to obtain reference numerals for use in describing the embodiments of FIG. 6, features which are the same as or which are analogous in structure or function to those depicted and described in FIGS. 1–3 are referenced with the same numeral used above, and increased by two-hundred (200). FIG. 6 illustrates a mug 40, which is illustrated as being transparent for purposes of convenience in description of the invention. However, the mug 40 need not be transparent. This mug 40 includes a lower or bottom surface 42. Attached to the bottom surface 42 by a layer of heat-conductive and heat-resistant adhesive 44 is a disk-shaped heating utensil 212. This utensil includes a shape-retaining body 228. Like the body 28 of the embodiment seen in FIGS. 1–3, the body 228 includes a matrix of shape-retaining, and non-conductive material 232, in which is substantially uniformly dispersed a microwave absorber material 234 (not visible in the drawing Figure), as was discussed above.

When the mug 40 and its contents are heated in a microwave oven, the utensil 212 heats much more efficiently than either the mug or the contents of this mug, if these contents are low in moisture content. Thus, the utensil generates heat and transfers this heat by conduction to the mug 40. Even when the mug contents are high in moisture content, and heat well in a microwave oven, the mug 40 instead of being heated solely or mostly by the heating of its contents and drawing heat out of these contents as usually is the case, instead is partially heated by the utensil 212.

That is, it will be recalled that most glass, ceramic and plastic materials from which the mug 40 may be fabricated do not heat well in a microwave oven. Thus, mugs which do not heat well but which themselves have a considerable thermal capacity can ordinarily draw a lot of heat out of their contents. By use of the utensil 212, this heating of the mug mostly be heating of the contents is mitigated. The utensil 212 enjoys a large ratio of heat transfer surface area with the mug 40 in comparison to the volume of the utensil, like the utensil 12 described above. Also, the utensil 212 liberates enough heat to assist in heating the contents of the mug. The net result is that with the same power setting of a microwave oven the contents of the mug 40 heats quicker than it would without the utensil 212.

FIG. 6 also depicts a spoon-like utensil 46 which is inserted into the contents of the mug 40 during heating in a microwave oven. The spoon-like utensil 46 and the utensil 212 may be used separately, and need not be used together. However, as depicted in FIG. 6, a cooperative advantageous result can be achieved if both these utensils are used together. The spoon-like utensil 46 includes a bowl portion 48 and a handle portion 50. The bowl and handle portions may or may not be molded or otherwise formed in one piece with one another. That is, the bowl portion, and at least part of the handle portion may be formed in one piece with the remainder of the handle portion being separately formed, if desired. However, importantly, the bowl portion 48 and a lower part 52 of the handle portion 50 (which part is immersed in liquid in the mug 40 when the spoon-like utensil is inserted into this mug) have substantially uniformly dispersed therein a microwave absorber material (not numbered in the drawing Figures but indicated with surface stippling) as was discussed above with respect to the embodiment of FIGS. 1–3. Thus, when the spoon-like utensil 46 is immersed in the liquid contents of a mug or other vessel and heated in a microwave oven, the utensil 46 heats and transfers this heat directly to the contents of the mug by conduction.

It will be apparent that a utensil, like the spoon-shaped utensil 46, which is directly immersed in the contents of a vessel during heating in a microwave oven need not be shaped like a spoon. For example, the reheating of a relatively low-moisture content food product, such as previously cooked pasta (like spaghetti, for example), in a microwave oven may take a considerable heating interval because of the relatively large energy capacity of the pasta and a relatively low moisture content for this food. A spoon-like or other such microwave absorber heating utensil may be immersed in the pasta, spaghetti, or other food to improve the efficiency of microwave absorption, and thereby to reduce the power setting or heating time interval required to prepare the food for consumption. That is, a direct-heating utensil for immersion in food may be shaped in a variety of convenient shapes for this use. A convenient shape for such use is that of a simple ball or spheroid. This article is easily removed from the food after heating and is also easily cleaned. One or more of such direct-heating utensils, whether shaped like a ball or in some other shape, may be dropped into a container or vessel of food prior to placing the vessel or container in a microwave oven. These utensils will assist in efficiently heating the food contents of the vessel or container, and can easily be removed prior to serving the heated food. Such ball-like utensils may be solid or hollow to control both their buoyancy as well as to control the ratio of heating volume (i.e., microwave absorbing volume) to surface area so that temperatures are controlled within the utensil (particularly at locations away from the heat transfer surface) under heating conditions. These utensils will be especially useful to improve the heating and shorten the heating time of low-moisture foods, as explained above.

Figure 8:
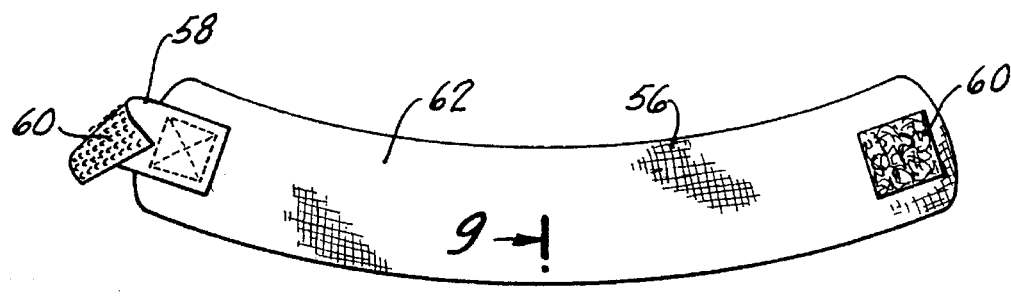

Further to the above, a microwave absorbing heating utensil may be shaped like a small ball or pellet. Such a utensil has utility for use in relatively large numbers in an appliance for therapeutic use as a hot pad or wrap. Advantageously, this hot pad or wrap may be immersed in water prior to heating in a microwave oven so that the advantages of a moist therapeutic heat are provided. By controlling the percentage of microwave absorber material present in the pellets, the temperature to which the appliance will heat in ovens of various power levels may be controlled. In this way, the user will not be burned or scalded by an over-heated appliance. Viewing now FIGS. 7–9, such an appliance in the form of a therapeutic hot-wrap for the neck is depicted. In FIG. 7, a human user 54 is depicted wearing a therapeutic hot wrap 56 in the form of a flexible collar-like article. The hot wrap 56 is adjustably secured by a length of web strap 58. As is seen in FIG. 8, the length of web strap 58 on its under side carries one component of a hook and loop fastener apparatus (generally indicated with the numeral 60), the other component of which is secured to the wrap 56 in the form of a small patch also indicated with the numeral 60. The wrap 56 includes a flexible body 62, which may be formed of fabric.

Figure 9:
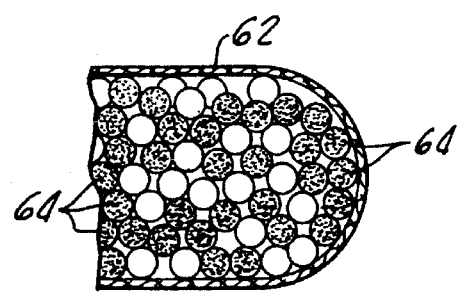

Viewing FIG. 9, it is seen that within the body 62 of fabric, the wrap 56 includes a multitude of pellets or comparatively small balls 64 of matrix material like that described above. These pellets or small balls 64 include a substantially uniform dispersion of the microwave absorbing heating material as was also discussed above. Importantly, the small balls or pellets cooperatively define a large wetted surface area and a considerable interstitial volume so that if the user chooses to enjoy moist heat, a simple immersion of the wrap 56 in water for a few seconds before heating is sufficient to add a considerable quantity of water to the wrap. Also importantly, the wrap 56 is not harmed by such immersion, unlike some conventional wraps for such uses which cannot be immersed nor washed after use. The wrap 56 can be so immersed, and may be washed and rinsed out should the fabric of the body 62 require. Of course, the wrap 56 may also be used dry should the user 54 prefer.

While the present invention has been depicted, described, and is defined by reference to particularly preferred embodiments of the invention, such reference does not imply a limitation on the invention, and no such limitation is to be inferred. The invention is capable of considerable modification, alteration, and equivalents in form and function, as will occur to those ordinarily skilled in the pertinent arts. For example, a flexible pouch fabricated of liquid-impermeable sheet material may be provided with a filling of microwave absorbing solid (i.e., pelletized or granular, for example) or liquid material. Such a pouch article may be used similarly to the utensils depicted in FIGS. 1 and 4 to heat dinner plates for food service thereon. These articles would be similar to the therapeutic wrap of FIGS. 7–9, configured in a thin disk shape with a liquid impermeable cover. Thus, the depicted and described preferred embodiments of the invention are exemplary only, and are not exhaustive of the scope of the invention. Consequently, the invention is intended to be limited only by the spirit and scope of the appended claims, giving full cognizance to equivalents in all respects.

We claim:

1. A microwave heating utensil particularly for heating dinner plates or other food-service or preparation vessels in a microwave oven, said utensil comprising: a thin and disk-like body of continuous matrix material, and a microwave absorber material dispersed substantially uniformly in said matrix material, upon exposure of said utensil to microwave energy said microwave absorber material heating and transferring heat to said matrix material, said body defining a heat-transfer surface sized for conducting heat outwardly of the utensil to a central portion of a dinner plate or other food-service or preparation vessel without substantially heating a rim portion thereof and having a large ratio of heat-transfer surface area to volume.

2. The microwave heating utensil of claim 1 wherein said body is flexibly shape-retaining.

3. The microwave heating utensil of claim 2 wherein said disk-like flexibly shape-retaining body includes a peripheral rim portion which is substantially free of said microwave absorber material.

4. The microwave heating utensil of claim 3 wherein said rim portion of said disk-like flexibly shape-retaining body is angulated relative to the remainder of said disk-like body so that said rim portion stands up off of the food-contacting surface of a dinner plate when said appliance is placed on a dinner plate for heating of the latter.

5. The microwave heating utensil of claim 2 wherein said flexibly shape-retaining body includes a matrix of silicone rubber.

6. The microwave heating utensil of claim 1 wherein said shape-retaining body includes a matrix material selected from the group including: silicone rubber, resinous polymer materials, and equivalents thereto.

7. The microwave heating utensil of claim 1 wherein said microwave absorber material includes a material selected from the group including graphite, iron, steel, ferrite, copper, aluminum, activated carbon, and carbon black.

8. The microwave heating utensil of claim 7 wherein said microwave absorber material is in a form selected from the group including: powder, filings, granules, fibers, and filaments.

9. The microwave heating utensil of claim 8 wherein said microwave absorber material has a size in the range from about 1 micron up to about 1 mm.

10. The microwave heating utensil of claim 9 wherein said microwave absorber material has a size less than 600 microns.

11. The microwave heating utensil of claim 1 wherein said microwave absorber material is present in said matrix material on a weight percentage basis of from about 1 percent to about 80 percent.

12. The microwave heating utensil of claim 1 wherein said utensil further included a heat-conductive and heat-resistant adhesive for attaching said utensil to a surface of a food preparation vessel.

13. A method of heating a dinner plate preparatory to the serving of food on the dinner plate for consumption, comprising the steps of:

providing a microwave-absorbing member which is configured to contact a central food-contacting portion of the dinner plate;

placing said microwave-absorbing member on the central food-contacting portion of the dinner plate, exposing the dinner plate and the microwave-absorbing member to microwave energy, using the microwave energy to heat the microwave-absorbing member and conducting heat from the microwave-absorbing member to the central food-contacting portion of the dinner plate to heat the latter; and maintaining a rim portion of the dinner plate substantially unheated.

\* \* \* \* \*